United States Patent [19]

Cheng et al.

[11] Patent Number: 4,866,179
[45] Date of Patent: Sep. 12, 1989

[54] PROCESS FOR THE MANUFACTURE OF PYRIDINE IN HIGH YIELD AND SELECTIVITY DURING A PROLONGED PERIOD OF OPERATION

[75] Inventors: Wan J. Cheng; Fu S. Lin; Yuh L. Jong; Fu J. Huang, all of Kaohsiung, Taiwan

[73] Assignee: Dairen Chemical Corporation, Taipei, Taiwan

[21] Appl. No.: 202,386

[22] Filed: Jun. 6, 1988

[51] Int. Cl.$^4$ .................................... C07D 213/08
[52] U.S. Cl. .................................... 546/250; 546/251
[58] Field of Search .................................... 546/250, 251

[56] References Cited

U.S. PATENT DOCUMENTS

| | | | |
|---|---|---|---|
| 3,272,825 | 9/1966 | Shimitzu et al. | 546/250 |
| 3,728,408 | 4/1973 | Tobias | 546/251 |
| 4,220,783 | 9/1980 | Chang et al. | 546/251 |
| 4,675,410 | 6/1987 | Feitter et al. | 546/251 |
| 4,701,529 | 10/1987 | Swearingen et al. | 546/251 |

FOREIGN PATENT DOCUMENTS

| | | |
|---|---|---|
| 51-144946 | 12/1976 | Japan . |
| 55-151558 | 11/1980 | Japan . |
| 55-151559 | 11/1980 | Japan . |
| 742643 | 12/1955 | United Kingdom . |
| 790994 | 2/1958 | United Kingdom . |

OTHER PUBLICATIONS

*Journal of Catalysis*, vol. 67, pp. 218–221 (1981).

Primary Examiner—Mary C. Lee
Assistant Examiner—E. Brendan Magrab
Attorney, Agent, or Firm—Sachs & Sachs

[57] ABSTRACT

An improved method of catalytic gaseous chemical synthesis of pyridine by reaction of ammonia and a carbonyl compound, preferably with added hydrogen, is described herein. The process employs as the catalyst a crystalline aluminosilicate zeolite which has been ion exchanged with a Group VIII metal of the Periodic Table. The preferred metal is palladium. Suitably, the Group VIII metal is present in an amount of about 0.01% to 5% by weight of the catalyst, preferably 0.1% to 2%. The crystalline aluminosilicate zeolite catalyst suitably has a silica to alumina mole rate of at least 15, preferably 30 to 200, and optimally, about 120 to 150. The process of the invention provides a high and selective yield of pyridine over a prolonged reaction period, and affords facile restorability of the catalyst.

23 Claims, No Drawings

PROCESS FOR THE MANUFACTURE OF PYRIDINE IN HIGH YIELD AND SELECTIVITY DURING A PROLONGED PERIOD OF OPERATION

BACKGROUND OF THE INVENTION

1. Field of the Invention

This invention relates to a process for the production of pyridine, and, more particularly, to an improved process for making pyridine in high yield and selectivity during a prolonged period of operation.

2. Discussion of the Relevant Art

Pyridine is an important chemical in the manufacture of agricultural chemicals, e.g. herbicides and pesticides, and, of various pharmaceuticals. Pyridine also is useful as a solvent in the polymer and textile industries.

Pyridine is obtained either as a by-product of the coal tar industry or by chemical synthesis by a catalytic gaseous reaction between ammonia and a carbonyl compond. However, pyridine is found in only small amounts in coal tar, and, in chemical synthesis, the low yields and poor selectively, and short operation cycle, and lifetime, of the catalytic process is disadvantageous. The use of such catalysts in the chemical synthesis of pyridine is described, for example, in U.K. Patent Nos. 790,994 and 742,743; and in U.S. Pat. No. 3,272,825. These synthetic methods involve the condensation reactions of ammonia or amines with aldehydes or ketones.

Amorphous aluminosilicate catalysts provide a reasonable yield of pyridine at the beginning of the process; however, after repeated operation cycles some limitations appear which make these catalysts unacceptable from a commercial standpoint. Specifically, (1) large amounts of carbonaceous deposits form which reduce the activity of the catalyst to below acceptable levels; (2) the selectively of the reaction for the desired pyridine and alkylpyridine becomes very poor; (3) the catalysts become thermally unstable; and (4) the activity of the used catalyst is difficult to restore completely by regeneration.

Crystalline aluminosilicate catalysts having a silica to alumina ratio of 12 to about 1000 and a constraint index within the range of 1 to 12 have been used instead of amorphous aluminosilicates in such reactions. See, e.g. U.S. Pat. Nos. 3,728,408; 4,220,783 and 4,675,410. These crystalline catalysts have been provided in an attempt to improve the performance of amorphous catalysts. However, the yield of pyridine, and selectivity operation life, and restorability of the catalyst after regeneration still has not been satisfactory. Specifically, the yield of pyridine is low, the ratio of pyridine to picolines is not suitable, and the yield of the desired pyridine product decreases sharply after several reaction/regeneration cycles.

SUMMARY OF THE INVENTION

An improved method of catalytic gaseous chemical synthesis of pyridine by reaction of ammonia and a carbonyl compound, preferably with added hydrogen, is described herein. The process employs as the catalyst a crystalline aluminosilicate zeolite which has been ion exchanged with a Group VIII metal of the Periodic Table. The preferred metal is palladium. Suitably, the Group VIII metal is present in an amount of about 0.01% to 5% by weight of the catalyst, preferably 0.1% to 2%. The crystalline aluminosilicate zeolite catalyst suitably has a silica to alumina mole ratio of at least 15, preferably 30 to 200, and, optimally, about 120 to 150.

The process of the invention provides a high and selective yield of pyridine over a prolonged reaction period, and affords facile restorability of the catalyst.

DESCRIPTION OF THE PREFERRED EMBODIMENTS

The catalytic gaseous chemical synthesis of pyridine herein is carried out by reaction of ammonia with a carbonyl compound. The carbonyl compound has from 1 to 5 carbon atoms therein, and may be a saturated or unsaturated compound. Suitable carbonyls include aldehydes and ketones, for example, formaldehyde, acetaldehyde, propionaldehyde, acrolein, crotonaldehyde, acetone and methylethyl ketone. Commercial forms of the carbonyl compound also may be used, including solutions in water, e.g. Formalin, which is an aqueous solutions of formaldehyde and a small amount of methanol. The carbonyl reactant may comprise a mixture of several carbonyl compounds, and these mixtures, if present, are preferably included in predetermined mole ratios of each carbonyl compound. For example, a formaldehyde: acetaldehyde mole ratio preferably is about 1:1.2 to about 1:2.2, while an acetaldehyde: acrolein mole ratio preferably is about 1:0.8 to about 1:1.4. The mole ratio of ammonia to the carbonyl compound usually is about 0.5 to about 30, and, preferably about 1 to about 10.

The reaction suitably is carried out at a temperature of 300 degrees to 600 degrees C., and, preferably, at 350 degrees to 550 degrees C. The gaseous reactants are reacted at a gas space velocity of about 200 to about 20,000/hour, and, preferably, at about 500 to 10,000/hour, at a pressure of about 0.2 to 20 atmospheres (atm.), and, preferably, at 0.8 to 10 atm. The reaction may proceed in a fixed bed, moving bed or fluidized bed reactor.

The crystalline aluminosilicate zeolite catalyst herein suitably has a silica to alumina mole ratio which is greater than 15, which will assure sufficient active acid sites favorable for the dehydration and dehydrogenation reactions between the carbonyl compound and ammonia. In addition, this ratio provides a catalyst having excellent temperature resistance. Preferably, the silica to alumina mole ratio is selected in the range of 30 to 200, and optimally, about 120 to 150.

The crystalline aluminosilicate zeolite catalyst of the invention preferably has other physical properties which will enhance its performance in the process herein. For example, the crystalline character of the zeolite should be consistent with a "Constraint Index" of about 4 to 12, as this parameter is defined and determined by the method of Frillette, in "Catalysis" by crystalline Aluminosilicates: Characterization of Intermediate Pore-Size Zeolites by the "Constraint Index", J. of Catalysis 67, 218–221 (1981), and references cited therein. The three dimensional crystal axis ratio (a:b:c) of these single crystal zeolites is about 1.5:1.5:1.

Other predetermined physical properties of the catalyst also will improve its performance. For example, a crystal density of greater than 1.6 g/cm$^3$, and a void volume of about 0.15 to 0.35 ml/ml-catalyst is desired. Furthermore, a particle size of greater than 0.5$\mu$ and less than 30$\mu$ provides a crystal surface area which will increase the yield and selectively for production of pyridine. The crystalline aluminosilicate zeolite catalysts for use herein are referred to in the art as ZSM and HZSM, the latter being the acid form which is the preferred form in the process of the invention. Typical commercial crystalline zeolites are ZSM-5 and HZSM-5.

Preferably, the sodium content in such zeolites is less than 0.2%. Any residual sodium present during manufacture of the zeolite can be removed easily by ion exchange in an ammonium salt solution, e.g. in $NH_4^+$ at 90 degrees C. for 4 hours, drying at 90 degrees C. and calcining at 500 degrees C. for 3 hours. This procedure also provides the hydrogen form of the zeolite.

To prepare the catalyst of the invention, the hydrogen form of the zeolite is ion exchanged in a solution of a Group VIII metal or metals, e.g. ruthenium, rhodium, palladium, osmium, iridium and platinum. Typically, palladium dichloride, ammonium hexchlororhodate, ammonium dichloroplatinate, and tetrammine palladium chloride. A palladium compound is preferred. The mixture is refluxed with stirring for 9 hours, filtered, and used, washed with deionized water until no chloride is detected, then dried in air at about 105 degrees C. to about 180 degrees C. for about 6 hours, particularly at about 120 to about 160 degrees C. Thereafter, the catalyst is calcinated at about 250 degrees C. to about 450 degrees C. for about 6 hours, particularly at about 300 degrees C. to about 350 degrees C. flushed with nitrogen, and reduced with hydrogen at about 450 degrees C. to about 650 degrees C., particularly at about 500 to about 600 degrees C.

The catalyst of the invention for synthesis of pyridine from an aldehyde or ketone has both dehydration and dehydrogenation properties. Such catalysts provide a high yield of pyridine and a high selectivity of pyridine compared to alkylpyridines. Catalysts with such bifunctional characteristics are obtained by ion exchange of zeolite with Group VIII metals.

The zeolite catalysts herein have the required dehydrogenation and dehydration bifunctional properties to prevent pore blocking, formation of high molecular weight pyridines, and carbon deposits, which make the operation period shorter, and require more time for catalyst regeneration. The Group VIII metal modified zeolites of the invention have a particularly suitable pore size and acidity to promote high selectivity to pyridine (and certain methyl pyridine e.g. alpha-picoline) a long operation life.

The Group VIII metal content of the crystalline aluminosilicate zeolite of the invention suitably is about 0.01% to about 5%, and preferably, about 0.1% to about 2%, by weight of the catalyst.

Moreover, to retard catalyst deactivation by coke formation, to prolong the reaction period and to facilitate catalyst regeneration, the reactants preferably are mixed with additional hydrogen gas, which is added as fresh hydrogen or recovered from the vent gases. A suitable concentration of hydrogen in the reaction mixture ranges from about 2% to about 200%, and preferably from about 10% to about 45% of the total mixture.

Binders, such as clay or silica, or metal oxide, e.g. aluminum oxide, magnesium oxide, zirconium oxide or titanium oxide, or mixtures thereof, may be included in the zeolite, suitably in an amount of about 25% to about 85% thereof, to predetermine its activity and to increase its temperature resistance.

The following examples will illustrate the invention more particularly.

EXAMPLE 1

50 g of ZSM-5 powders having a silica:alumina ratio of about 150:1 and a crystal size of about 2–4μ was converted to the H-form by ion exchange under reflux in a 2.5N $NH_4NO_3$ solution for 4 hours at 90 degrees C. The resulting product was washed, dried at 105 degrees C. and calcinated in air at 560 degrees C. for 4 hours. The HZSM-5 zeolite then was refluxed in 200 ml. of 0.13% $PdCl_2$ solution for 9 hours, filtered, washed with deionized water until no chloride could be detected, dried at 110 degrees C., calcinated at 350 degrees C. for 6 hours, reduced at 500 degrees C. with hydrogen for 4 hours. The thus-treated zeolite then was loaded into a 22 mm. diameter fluid bed reactor and heated under an ammonia flow of 130 liters per hour to a temperature of 430 degrees C. for 2 hours. A mixture of 51.5 g of acetaldehyde, 60 g of formalin (42% formaldehyde) and 30 liters of hydrogen per hour then was admitted through a vaporizer into the reactor. After a predetermined reaction period, the products were condensed and analyzed. The results are shown in Table 1 below.

TABLE 1

| Catalyst PdZSM-5 $SiO_2:Al_2O_3 = 150$ | | | | |
|---|---|---|---|---|
| Time on stream, hrs. | 0.5 | 4 | 50 | 100 |
| Pyridine yield, mol % | 85.5 | 87.7 | 84.6 | 83.9 |
| Pyridine/β-picoline | 7.90 | 8.24 | 8.35 | 8.51 |
| Pyridine/α-picoline | 38.5 | 40.2 | 44.7 | 49.4 |

EXAMPLE 2

The procedure of Example 1 was repeated except that the HZSM-5 zeolite was refluxed in 200 ml. of 0.52% ammonium hexchlororhodate solution. The results are shown in Table 2.

TABLE 2

| Catalyst RhZSM-5 $SiO_2:Al_2O_3 = 150$ | | | | |
|---|---|---|---|---|
| Time of stream, hrs. | 0.5 | 4 | 50 | 100 |
| Pyridine yield, mol % | 84.3 | 85.2 | 85.0 | 84.8 |
| Pyridine/β-picoline | 9.21 | 9.33 | 9.54 | 9.67 |
| Pyridine/α-picoline | 43.5 | 45.6 | 53.6 | 57.4 |

EXAMPLE 3

The procedure of Example 1 was repeated except that the HZSM-5 was refluxed in 200 ml. of 0.52% ammonium dichloroplatinate solution. The results are shown in Table 3.

TABLE 3

| Catalyst PtZSM-5 $SiO_2:Al_2O_3 = 150$ | | | | |
|---|---|---|---|---|
| Time on stream, hrs. | 0.5 | 4 | 50 | 100 |
| Pyridine yield, mol % | 83.2 | 84.3 | 84.5 | 84.5 |
| Pyridine/β-picoline | 8.79 | 8.81 | 8.83 | 8.87 |
| Pyridine/α-picoline | 41.2 | 42.1 | 42.4 | 43.2 |

EXAMPLE 4

Example 3 was repeated after ten reaction/regeneration/reduction cycles. The results are shown in Table 4.

TABLE 4

| Catalyst PtZSM-5 $SiO_2:Al_2O_3 = 150$ | | | | |
|---|---|---|---|---|
| Time of stream, hrs. | 0.5 | 4 | 50 | 100 |
| Pyridine yield, mol % | 83.0 | 83.9 | 83.5 | 82.7 |
| Pyridine/β-picoline | 8.96 | 8.98 | 9.45 | 9.92 |

TABLE 4-continued

| Pyridine/α-picoline | 43.2 | 43.5 | 45.4 | 47.2 |

EXAMPLE 5

The procedure of Example 1 was followed except that acetaldehyde, acrolein, ammonia and hydrogen were reacted at selected flow rates in a fluidized bed reactor. The results are shown in Table 5.

TABLE 5

Catalyst PdZSM-5 $SiO_2:Al_2O_3 = 150$

| Reaction temperature, degrees C. | | 470 | |
|---|---|---|---|
| Acetaldehyde | g/hr | 116.6 | |
| Acrolein | g/hr | 134.4 | |
| Ammonia | l/hr | 245 | |
| hydrogen | l/hr | 74 | |
| Time on stream, hrs. | | 4 | 50 |
| Pyridine yield, mol % | | 69.7 | 69.6 |
| Pyridine/β-picoline | | 10.8 | 11.3 |
| Pyridine/α-picoline | | 50.2 | 53.3 |

EXAMPLE 6

Following the procedure of Example 1, crotonaldehyde, formalin, ammonia and hydrogen were reacted at selected flow rates in a fluidized bed reactor. The results are shown in Table 6.

TABLE 6

Catalyst PdZSM-5 $SiO_2:Al_2O_3 = 150$

| Reaction temperature, degrees C. | | 460 | |
|---|---|---|---|
| Crotonaldehyde | g/hr | 53 | |
| Formaldehyde | g/hr | 30 | |
| Ammonia | l/hr | 80 | |
| hydrogen | l/hr | 50 | |
| Water | g/hr | 72 | |
| Time on stream, hrs. | | 4 | 50 |
| Pyridine yield, mol % | | 72.4 | 71.5 |
| Pyridine/β-picoline | | 12.5 | 13.2 |
| Pyridine/α-picoline | | 52.7 | 54.9 |

EXAMPLE 7

PtZSM-5 zeolite, as produced in Example 3, was extruded into a cylinder having a 1/16 inch diameter and a 1/5 inch length using 30% alumina as a binder. The catalyst article then was heated for 4 hours at 580 degrees C. 100 g of the thus-heated catalyst then was charged in a quartz reactor having an 18 mm. internal diameter. The catalyst was purged under $NH_3$ at 470 degrees C. for 2 hours, and acetaldehyde, formalin (42%), hydrogen and water were fed into the reactor at rates of 106 g, 45 g, 451 g, and 107 g per hour, respectively. After a predetermined reaction period, the yield of products were determined using gas chromatography. The results are shown in Table 7.

TABLE 7

Catalyst PtZSM-5 $SiO_2:Al_2O_3 = 150$

| Time on stream, hrs. | 4 | 50 |
|---|---|---|
| Pyridine yield, mol % | 72.4 | 71.5 |
| Pyridine/β-picoline | 9.12 | 9.87 |
| Pyridine/α-picoline | 78.4 | 82.1 |

EXAMPLE 8 (COMPARATIVE)

The reaction conditions of Example 1 were used except that HZSM-5 was the catalyst and no hydrogen was added. The results are shown in Table 8.

TABLE 8

Catalyst HZSM-5 $SiO_2:Al_2O_3 = 150$

| Time on stream, hrs. | 0.5 | 4 | 50 | 100 |
|---|---|---|---|---|
| Pyridine yield, mol % | 75.5 | 74.9 | 62.8 | 41.5 |
| Pyridine/β-picoline | 2.15 | 2.22 | 2.34 | 2.51 |
| Pyridine/α-picoline | 13.5 | 14.2 | 15.7 | 18.4 |

The results in Table 8 show that reduced pyridine yields and poorer selectivity are obtained in the absence of metal of the present invention in the zeolite catalyst.

EXAMPLE 9 (COMPARATIVE)

Example 7 was repeated using PtZSM-5, but without supplementary hydrogen. The results are shown in Table 9.

TABLE 9

Catalyst PtZSM-5 $SiO_2:Al_2O_3 = 150$

| Time on stream, hrs. | 4 | 50 |
|---|---|---|
| Pyridine yield, mol % | 65.7 | 50.2 |
| Pyridine/β-picoline | 2.31 | 2.71 |
| Pyridine/α-picoline | 13.9 | 22.8 |

Table 9 shows that in the absence of added hydrogen in the reactant mixture, a reduced yield of pyridine and poor selectivity is obtained.

EXAMPLE 10

The reactions of Examples 1, 7, 8 and 9 were carried out for a period of 50 hours. The catalysts then were purged with nitrogen and regenerated with a gaseous mixture of air and nitrogen. The maximum temperature of the reactor was kept at about 500 degrees C. by gradually increasing the oxygen concentration until no $CO_2$ was detected in the vent gas. After a predetermined reduction period, the vent gases were analyzed. The results which are shown in Table 10 demonstrate that catalysts which were modified with Group VIII metals, and which were used in a suitable concentration of hydrogen in the reaction mixture, were regenerated most easily.

TABLE 10

| Catalyst Example No. | PdZSM-5 (powder) 1 | PtZSM-5 (extruded) 7 | HZSM-5 (extruded) 8 | PtZSM-5 (extruded) 9 |
|---|---|---|---|---|
| Reactant with addition of hydrogen | Yes | Yes | No | No |
| Regeneration Time (Hours) | Inlet $O_2$ (%) | Vent Gas $CO_2$ (%) | | |
| 2 | 1 | 0.89 | 0.80 | 0.43 | 0.39 |
| 6 | 2 | 1.67 | 1.43 | 0.92 | 0.88 |
| 10 | 4 | 2.64 | 2.41 | 1.79 | 1.54 |
| 16 | 8 | 5.48 | 4.79 | 3.17 | 2.85 |
| 24 | 10 | 0.01 | 0.02 | 4.57 | 3.79 |
| 48 | 16 | Trace | Trace | 0.23 | 0.19 |
| 72 | 21 | — | — | 0.01 | 0.02 |

Although the invention has been described with reference to certain embodiments thereof, it will be understood that changes and modifications may be made which are within the skill of the art. It is intended to be bound only by the appended claims:

What is claimed is:

1. A process for producing pyridine which comprises effecting catalytic gaseous reaction between ammonia and a carbonyl compound reactant in the presence of a catalyst which is a crystalline aluminosilicate zeolite which has been ion exchanged with a Group VIII metal of the Periodic Table selected from palladium, rhodium and platinum, and hydrogen is included in said reactant mixture in an amount of from about 2% to about 200% of the mixture.

2. A process according to claim 1 in which said metal is palladium.

3. A process according to claim 1 which said Group VIII metal is mixed with another metal of group VIII.

4. A process according to claim 1 in which said Group VIII metal is present in an amount of about 0.01% to about 5% by weight of the crystalline aluminosilicate zeolite.

5. A process according to claim 1 in which said metal is present in an amount of about 0.1% to about 2% by weight of said crystalline aluminosilicate zeolite.

6. A process according to claim 1 in which said hydrogen is present in an amount of from about 10% to about 45%.

7. A process according to claim 1 in which said catalyst has a silica to alumina mole ratio of at least 15.

8. A process according to claim 7 in which said catalyst has a silica to alumina mole ratio of about 30 to 200.

9. A process according to claim 7 in which said catalyst has a silica to alumina mole ratio of about 120 to 150.

10. A process according to claim 1 in which said zeolite is ZSM-5.

11. A process according to claim 1 in which said zeolite is HZSM-5.

12. A process according to claim 1 in which said carbonyl compound is a saturated or unsaturated aldehyde or ketone having from 1 to 5 carbon atoms.

13. A process according to claim 10 in which said carbonyl compound is selected from acetaldehyde, formaldehyde, crotonaldehyde, or acrolein, and mixtures and solutions thereof.

14. A process according to claim 1 in which the reaction is carried out in a fixed, moving or fluidized bed reactor.

15. A process according to claim 1 in which the reaction is carried out at a temperature of about 300 to 600 degrees C., a gas pressure of about 0.2 to 20 atm. and a gas velovity of about 200 to 20,000 1/hr.

16. A process according to claim 15 in which the temperature is about 350 to 550 degrees C., the pressure is about 0.8 to 10 atm. and the gas velocity is about 500 to 10,000 1/hr.

17. A process according to claim 1 in which the mole ratio of ammonia to the carbonyl reactant is about 0.5 to 30.

18. A process according to claim 17 in which said mole ratio is about 1 to 10.

19. A process according to claim 12 in which the carbonyl reactant is a mixture of acetaldehyde and formaldehyde.

20. A process according to claim 12 in which the carbonyl reactant is a mixture of acetaldehyde and formaldehyde.

21. A process according to claim 12 in which the carbonyl reactant is a mixture of crotonaldehyde and formaldehyde.

22. A process according to claim 12 in which the carbonyl reactant is a mixture of acetaldehyde and acrolein.

23. A process for the production of pyridine which comprises effecting catalytic gaseous reaction between ammonia and a carbonyl compound in the presence of a catalyst which is a crystalline aluminosilicate which has been ion exchanged with palladium, rhodium or platinum, in an amount of about 0.01% to about 5% by weight of the catalyst, and hydrogen is included in the reactant mixture in an amount of about 2% to about 200% of the mixture.

* * * * *